United States Patent [19]

Hsieh

[11] Patent Number: 5,741,290
[45] Date of Patent: Apr. 21, 1998

[54] EYEBROW TATTOOING TOOL

[75] Inventor: Ta-Ching Hsieh, Taipei, Taiwan

[73] Assignee: Te-Shih Huang, Pan Chiao, Taiwan

[21] Appl. No.: 541,560

[22] Filed: Oct. 10, 1995

Related U.S. Application Data

[63] Continuation-in-part of Ser. No. 290,328, Aug. 15, 1994, abandoned.

[51] Int. Cl.⁶ .................................................. A61B 17/34
[52] U.S. Cl. ................................... 606/186; 606/185
[58] Field of Search ....................... 606/116, 184–189; 604/19, 22

[56] References Cited

U.S. PATENT DOCUMENTS 4,914,988 4/1990 Chang .................................. 606/186

*Primary Examiner*—Glenn K. Dawson
*Attorney, Agent, or Firm*—Pro-Techtor International Services

[57] ABSTRACT

An eyebrow tattooing tool for marking make-up designs on the eyebrow. The eyebrow tattooing tool is composed of multiple disposable parts that can be easily assembled and disassembled in case any parts are tainted with blood from the person being tattooed so as to prevent blood-transmitted diseases from transmitting from person to person. In the eyebrow tattooing tool, the pigment liquid can be prevented from flowing backward to the motor so as to protect the motor from being damaged thereby. The multiple disposable parts allow the eyebrow tattooing tool to be used in a sanitary way and also allow long-term economic use of the eyebrow tattooing tool by replacing only the parts that are tainted without having to dispose of the whole of the eyebrow tattooing tool.

4 Claims, 5 Drawing Sheets

EYEBROW TATTOOING TOOL

This is a continuation-in-part application of the U.S. patent application Ser. No. 08/290,328 filed on Aug. 15, 1994, now abandoned.

BACKGROUND OF THE INVENTION

1. Field of the Invention

The present invention relates to tattooing tools, and more particularly, to an eyebrow tattooing tool for marking make-up designs on the eyebrow.

2. Description of Prior Art

An eyebrow tattooing tool is an implement used to mark make-up designs on the eyebrow by making punctures in it and inserting pigments. It is usually small in size for easy operation. A prior art eyebrow tattooing tool is as shown in FIGS. 5 and 6, in which a motor 60 housed in a casing 1 is used to drive a needle cannula 80 for reciprocating motion through the transmission via a shaft 70 and crank arm 71. The reciprocating motion of the needle cannula 80 thereby allows the eyebrow tattooing tool to make punctures on the skin of the eyebrow and insert pigments therein. Since the needle cannula could be soaked with blood through the punctures, both the needle cannula 80 and the front cap 62 that secures the cannula 80 are made disposable in order to prevent such blood-transmitted infectious diseases as AIDS and hepatitis from transmitting via the eyebrow tattooing tool from person to person.

However, it is a drawback of the prior art eyebrow tattooing tool that, since the eyebrow skin is punctured to the hypodermis, blood could flow through the pore of the needle cannula by means of capillary effect to the shaft 70. Although it is a common practice that new needle cannula is to replace the used one when tattooing the next person, the blood from the previously tattooed person and amassed around the shaft 70 could be conveyed via the new needle cannula into the body of the next person to be tattooed. Blood-transmitted infectious diseases as AIDS and hepatitis could therefore still be transmitted from person to person via the prior art eyebrow tattooing tool.

It is another drawback of the prior art eyebrow tattooing tool that, although the needle cannula 80 and the front cap 62 are disposable after each use, the pigment liquid could flow by means of capillary effect through the needle cannula 80 into the front cap 62. After a long time of use, the inside of the front cap 62 would be eventually accumulated with lumps of half-dried pigments, thus hindering the reciprocating motion of the needle cannula 80 that passes through the inside of the front cap 62. The operation of the eyebrow tattooing tool would therefore be difficult to perform. Moreover, part of the pigment liquid could flow along the inner wall of the front cap 62 to the inside of the intermediate casing 63 and spread everywhere around the shaft 70 as illustrated by the dotted pattern in FIG. 5. Since the eyebrow tattooing tool is usually held with the needle cannula 80 pointed upwards during the tattooing, the pigment liquid could flow via the shaft 70 to the motor 60, thus causing the motor 60 to malfunction or to rust.

SUMMARY OF THE INVENTION

It is therefore a primary objective of the present invention to provide an eyebrow tattooing tool in which the pigment would not be amassed in the front cap to hinder the reciprocating motion of the needle cannula.

It is another objective of the present invention to provide an eyebrow tattooing tool in which the pigment liquid can be prevented from flowing backward to the motor.

It is still another objective of the present invention to provide an eyebrow tattooing tool which is composed of multiple disposable parts such that blood-soaked parts or pigment-amassed parts can be replaced with new ones whenever needed to do so.

In accordance with the foregoing and other objectives of the present invention, there is provided a novel eyebrow tattooing tool. The eyebrow tattooing tool comprises (a) a needle cannula for making punctures; (b) a transmission shaft coupled to the needle cannula, the transmission shaft comprising a front section coupled by means of a first coupling to the needle cannula, an intermediate section coupled by means of a second coupling to the front section, and a rear section coupled by means of a third coupling to the intermediate section; (c) means, coupled to the rear section of the transmission shaft for driving the transmission shaft for reciprocating motion; (d) a casing for housing the driving means; (e) a front cap for housing the needle cannula; (f) a rear cap, coupled by means of a fourth coupling to the front cap, for housing the front section of the transmission shaft; and (g) a locking member, coupled by means of a fifth coupling to the rear cap and by means of a sixth coupling to the casing, for securing the rear cap to the casing.

In the eyebrow tattooing tool set forth above, the first coupling, the second coupling, the third coupling, the fourth coupling, the fifth coupling, and the sixth coupling are detachable by hand so as to make the needle cannula, the front section, the intermediate section, the rear section of the transmission shaft, the front cap, the rear cap, and the locking member disposable.

BRIEF DESCRIPTION OF DRAWINGS

The present invention can be more fully understood by reading the subsequent detailed description of the preferred embodiments thereof with references made to the accompanying drawings, wherein.

DETAILED DESCRIPTION OF PREFERRED EMBODIMENT

Figure 1:
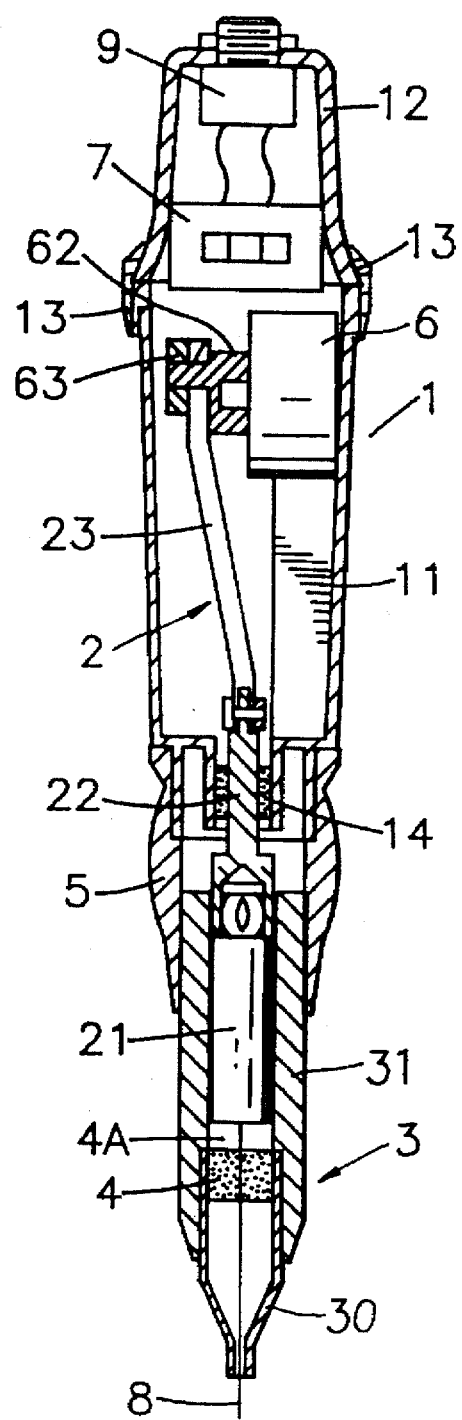
FIG. 1 shows a longitudinal sectional view of the first preferred embodiment of the eyebrow tattooing tool according to the present invention.
Figure 2:
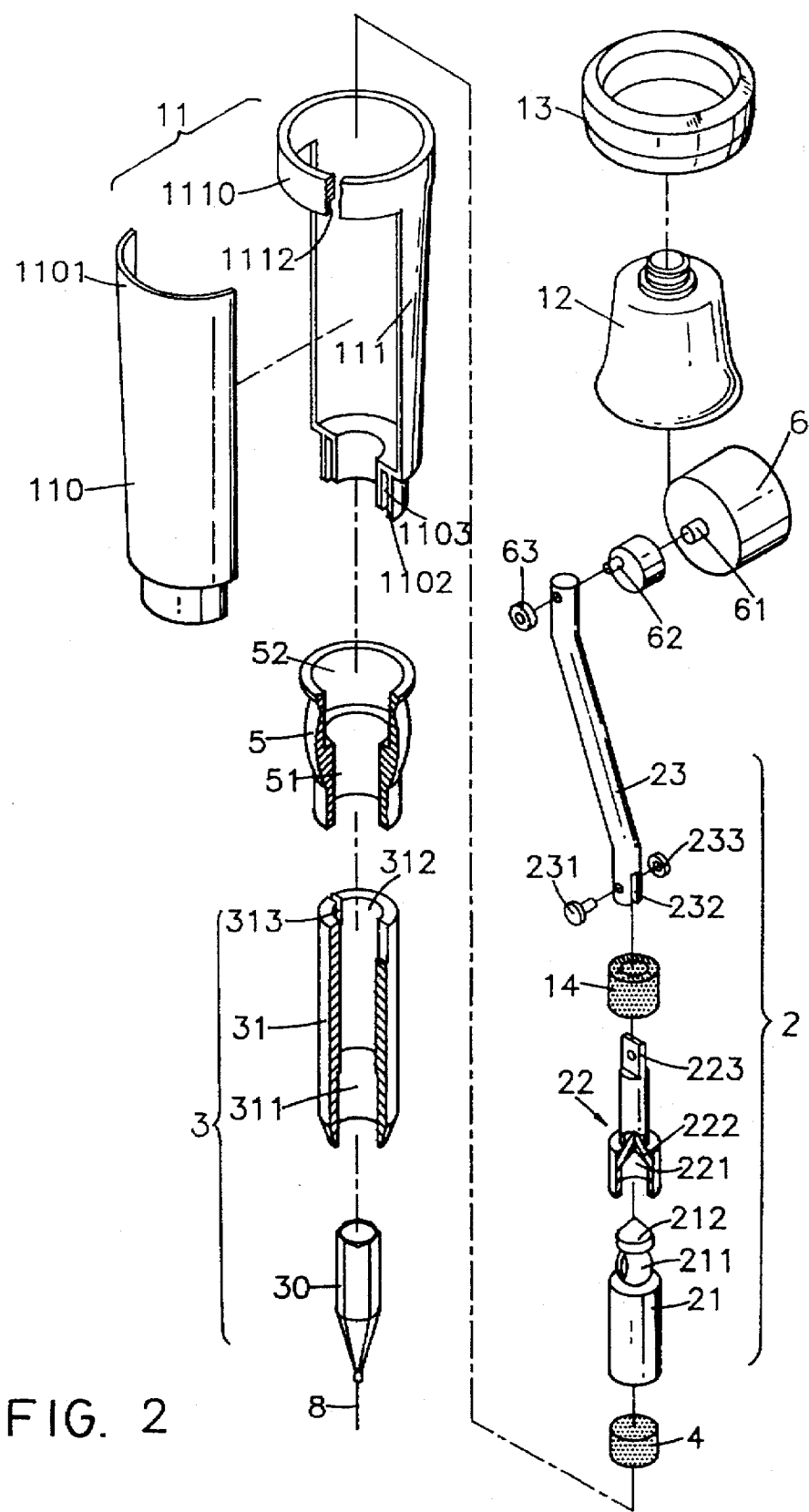
FIG. 2 shows an exploded perspective view of the eyebrow tattooing tool of FIG. 1.

Referring to FIGS. 1 and 2, the eyebrow tattooing tool according to the present invention is composed of a casing 1, a three-section transmission shaft 2, a cap 3, a pigment absorber 4, a locking member 5, a motor 6, a switch 7, a needle cannula 8, and a socket 9. The casing is further composed of three parts: a front casing 11, a rear casing 12, and a coupler 13 coupling the front casing 11 and the rear casing 12. The motor 6 is housed at the rear end of the front casing 11 and the switch 7 and the socket 9 are housed in the rear casing 12. The front casing 11 is further composed of a replaceable top portion 110 and a fixed bottom portion 111. The replaceable top portion 110 is fastened to rear portion 1101 of the replaceable top portion 110 by means of a protruded portion 1112 on the rim 1110 on the rear end of the fixed bottom portion 111. This allows the user of the eyebrow tattooing tool to remove the replaceable top portion 110 so as to disassemble the linkage between the three-section transmission shaft 2 and the motor 6.

The three-section transmission shaft 2 is composed of three sections: a front section 21, an intermediate section 22, and a rear section 23. A needle cannula 8 is inserted into the front section 21 and the rear section 23 is pivotally coupled via an eccentric disk 62 and securing member 63 to the shaft 61 of the motor 6. The front section 21 is fastened to the intermediate section 22 by means of the insertion of an elastic member 211 on the 21 into a hole 221 on the intermediate section 22, and the intermediate section 22 is fastened to the rear section 23 by means of a bolt 231 and a nut 233. To prevent the transmission shaft from vibration, a buffering member 14 as sponge is further positioned between the front end 1103 of the front casing 11 and the intermediate section 22.

As illustrated in the drawings, the front cap 30 is combined with the rear cap 31 by means of insertion into the front opening 311 of the rear cap 31. Whenever replacement is required, the front cap 30 can be separated from the rear cap 31 simply by pulling these two parts apart by hand. A locking member 5 is used to secure the rear cap 31 along with the front cap 30 holding the needle cannula 8 in front position of the eyebrow tattooing tool. The coupling between the locking member 5 and the rear cap 31 is by insertion of an insertion member 313 on the rear cap 31 into the reception hole 51 of the locking member 5, the depth of the insertion being adjustable so as to adjust the overall length of the eyebrow tattooing tool for easy operation. The locking member 5 is secured to the front casing 11 by means of the insertion of the rear bore 52, which is slightly larger in diameter than the front bore 51, to a cylindrical coupler 1102 on the front casing 11. Onwards, the front casing 11 is combined with the rear casing 12 by means of an elastic jacket 13. All of the couplings between front cap 30 and rear cap 31, rear cap 31 and locking member 5, locking member 5 and front casing 11, and front casing 11 and rear casing 12 are individually detachable by pulling them apart slightly forcibly by hand.

It is an important aspect of the present invention that, in order to prevent pigment liquid from flowing reversibly to the motor 6, a pigment absorber 4, which can be any liquid absorbing material as sponge, fibrous material, and paper tissue, is provided inside the front cap 30 to surround a rear segment of the needle cannula 8. In addition, a space 4A (see FIG. 1) is left between the pigment absorber 4 and the front section 21 of the transmission shaft 2 so that the pigment absorbed in the pigment absorber 4 is prevented from touching the front section 21 of the transmission shaft 2 and onwards being drawn backwards to the motor 6.

Figure 3:
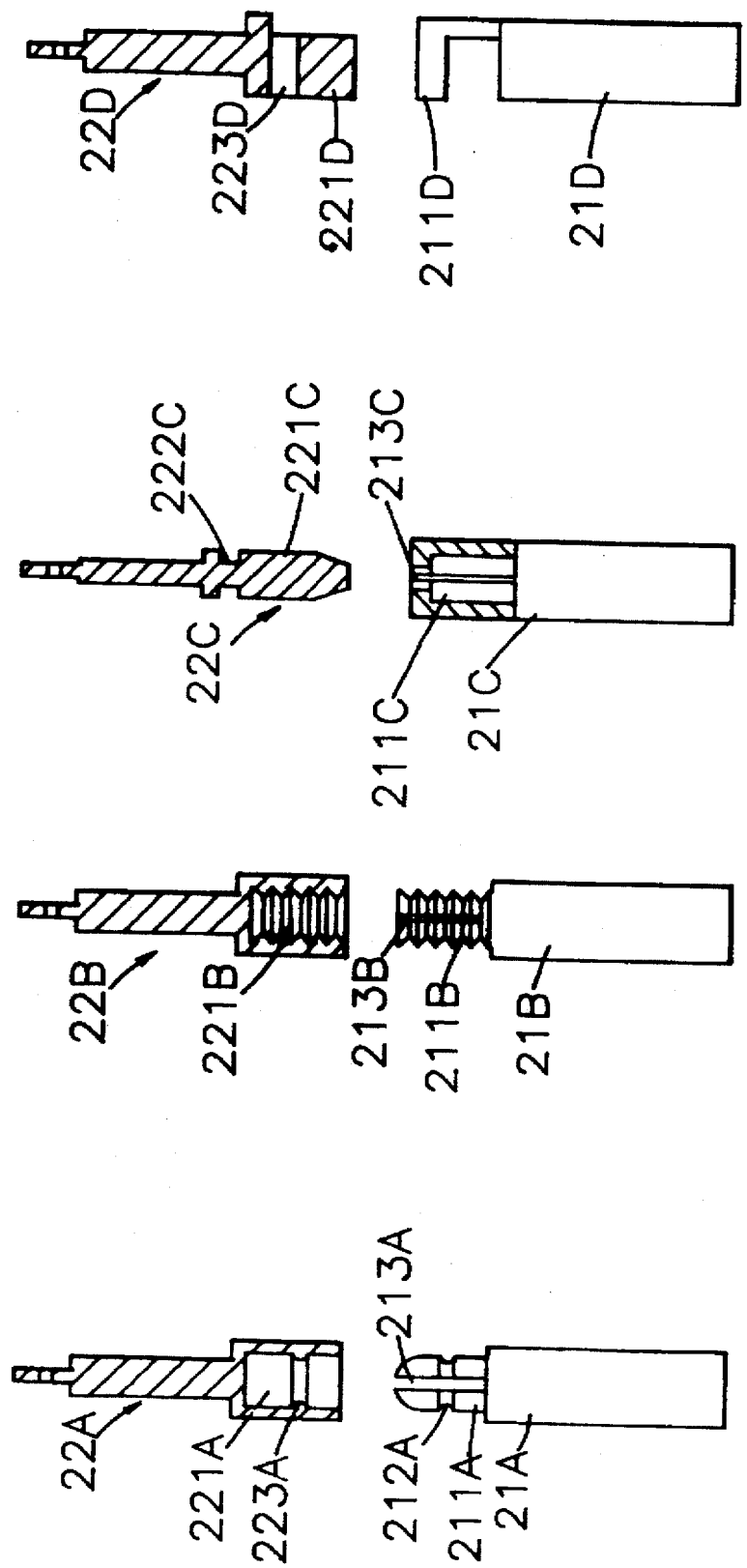
FIGS. 3A–3D show four additional embodiments of a linkage employed in the eyebrow tattooing tool according to the present invention.

There are various modifications to the coupling between the front section 21 and intermediate section 22 of the transmission shaft 2 as those illustrated in FIGS. 3A–3D. In FIG. 3A, the front section 21A is provided with an insertion member 211A consisting of two split elastic pieces 213A and having a small-diameter portion 212A for insertion into a reception hole 221A on the intermediate section 22A. A constricted portion 223A in the reception hole 221A couples to the small-diameter portion 212A so as to secure the insertion member 211A in position. In another modification shown in FIG. 3B, the front section 21B is provided with a male threaded portion 211B with a split 213B and the intermediate section 22B is provided with a female threaded portion 221B to couple the front section 21B to the intermediate section 22B. In still another modification shown in FIG. 3C, the intermediate section 22C is provided with an insertion member consisting of a tapered head portion 221C and a constricted neck portion 222C and the front section 21C is provided with a reception portion 211C consisting of two split elastic pieces 213C. In still yet another modification shown in FIG. 3D, the front section 21D is formed with an L-shaped piece 211D and the intermediate section 22D is provided with a reception hole 223D with about the same dimensions as the L-shaped piece 211D.

It is a primary benefit of the eyebrow tattooing tool according to the present invention that all the constituent parts including the casing 1 (including front casing 11 and rear casing 12), the cap 3, the pigment absorber 4, the locking member 5, the needle cannula 8, and the front section 21, intermediate section 22, and rear section 23 of the transmission shaft 2 attachable to and detachable from the assembly so as to be disposed of and replaced with new ones. This allows any part of the eyebrow tattooing tool that is tainted with blood to be disposal without having to dispose of the whole of the eyebrow tattooing tool as using the prior art.

Figure 4:
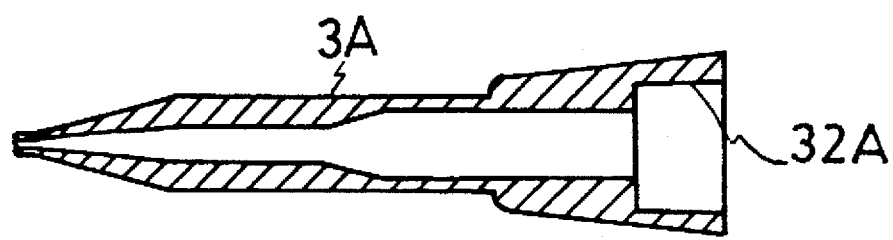
FIG. 4 shows a longitudinal sectional view of a constituent part of the eyebrow tattooing tool according to the present invention.
Figure 5:
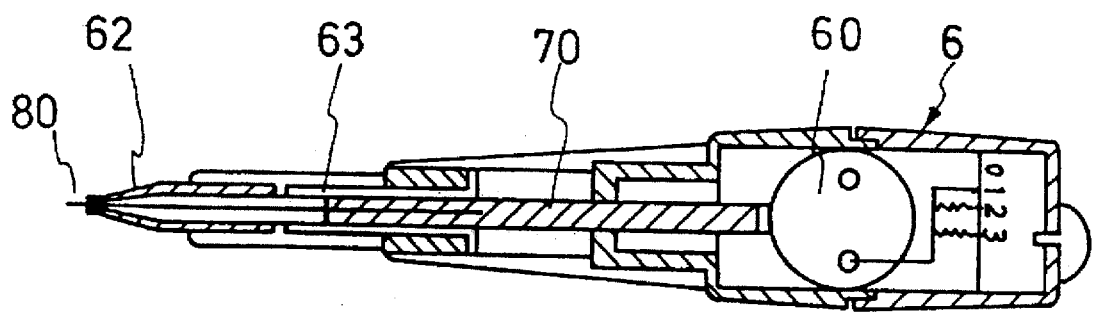
FIG. 5 shows a longitudinal sectional view of a prior art eyebrow tattooing tool.
Figure 6:
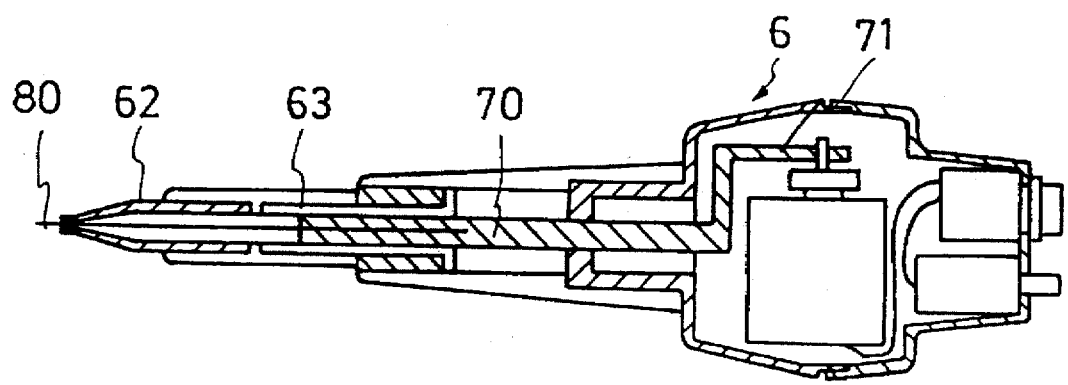
FIG. 6 shows another longitudinal sectional view of the prior art eyebrow tattooing tool of FIG. 5.

As shown in FIG. 4, in the second embodiment of the eyebrow tattooing tool, the front cap 30, the rear cap 31, and the locking member 5 are integrally formed into a single piece 3A, which is to be coupled to the front casing 11 by means of a reception hole 32A formed at the rear end. This embodiment allows the reduction of the number of constituent parts for the eyebrow tattooing tool. Moreover, the reception hole 32A can be shaped in square or polygon in cross section that matches the circular circumference of the cylindrical coupler 1102 on the front casing 11 such that the coupling can be made more tightly secured.

Similarly, the front cap 30 can have its periphery shaped into a hexagon or octagon in cross section that matches the circumference of the front end of the rear cap 31, and the rear cap 31 can have its rear end formed with two split elastic pieces 313 for insertion into the reception hole 51 on the locking member 5. The depth of the insertion of the split elastic pieces 313 into the reception hole 51 can be adjusted so as to adjust the length of the part of the needle cannula exposed to the outside of the front cap 30.

Also, the locking member 5 can have its rear end formed into a square or polygon in cross section so as to allow the coupling between the front cap 30 and rear cap 31 and the coupling between the locking member 5 and the front casing 11 to be made by means of forcible exertion of the sides of the polygon-shaped against the inner wall. This provision allows air flow path to be left between the coupling so that detachment can be made easier and capillary effect through the needle cannula and the front cap 30 can be prevented.

The present invention has been described hitherto with exemplary preferred embodiments. However, it is to be understood that the scope of the present invention need not be limited to the disclosed preferred embodiments. On the contrary, it is intended to cover various modifications and similar arrangements within the scope defined in the following appended claims. The scope of the claims should be accorded the broadest interpretation so as to encompass all such modifications and similar arrangements.

What is claimed is:

1. An eyebrow tattooing tool, comprising:
   (a) a needle cannula for making punctures;
   (b) a transmission shaft comprising a front section detachably inserted coupled to said needle cannula, an intermediate section detachably inserted to the front section, and a rear section detachably fixed to the intermediate section;
   (c) a driving means detachably coupled to the rear section of said transmission shaft for driving said transmission shaft for reciprocating motion;
   (d) a casing having a front casing and a rear casing for housing said driving means, a switch for controlling said driving means and a socket detachably connected to a power supply;
   (e) a front cap housing said needle cannula;
   (f) a rear cap detachably engaging with said front cap, for housing the front section of said transmission shaft; and
   (g) a locking member detachably connected to said rear cap and securing said rear cap to said casing;
   wherein said needle cannula, the front section, the intermediate section, the rear section of said transmission shaft, said front cap, said rear cap, and said locking member are detachable and disposable; and
   wherein the front section is detachably inserted into the intermediate section of said transmission shaft and comprises:
      an insertion member consisting of two split elastic pieces and having a small-diameter portion; and the intermeditate section comprises
      a reception hole, said reception hole having a constricted portion detachably coupled to the small-diameter portion of said insertion member so as to secure the insertion member in position.

2. An eyebrow tattooing tool as set forth in claim 1, wherein the front section is detachably inserted into the intermediate section of said transmission shaft and comprises:
   a male threaded portion; and the intermeditate section comprises
   a female threaded portion.

3. An eyebrow tattooing tool as set forth in claim 1, wherein the front section is detachably inserted into the intermediate section of said transmission shaft and comprises:
   a L-shaped piece on the front section; and
   a reception hole.

4. An eyebrow tattooing tool as set forth in claim 1, wherein the front section is detachably coupled to the intermediate section of said transmission shaft, the intermediate section comprising:
   an insertion member consisting of a tapered head portion and a constricted neck portion; and the front section comprising:
   a reception portion consisting of two split elastic pieces.

* * * * *